(12) United States Patent
Vantard et al.

(10) Patent No.: US 9,144,639 B2
(45) Date of Patent: Sep. 29, 2015

(54) DIALYSIS APPARATUS AND METHOD FOR CONTROLLING A DIALYSIS APPARATUS

(75) Inventors: Georges Vantard, Villefontaine (FR); Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 322 days.

(21) Appl. No.: 13/642,404

(22) PCT Filed: Apr. 14, 2011

(86) PCT No.: PCT/IB2011/000829
§ 371 (c)(1),
(2), (4) Date: Jan. 22, 2013

(87) PCT Pub. No.: WO2011/132046
PCT Pub. Date: Oct. 27, 2011

(65) Prior Publication Data
US 2013/0116650 A1    May 9, 2013

(30) Foreign Application Priority Data

Apr. 19, 2010   (EP) .................................. 10004110

(51) Int. Cl.
*A61M 1/16* (2006.01)
*A61M 1/34* (2006.01)
(Continued)

(52) U.S. Cl.
CPC ............... *A61M 1/1656* (2013.01); *A61M 1/16* (2013.01); *A61M 1/1607* (2014.02); *A61M 1/1609* (2014.02); *A61M 1/1613* (2014.02); *A61M 1/1617* (2014.02); *A61M 1/1647* (2014.02); *A61M 1/3403* (2014.02); *A61M 5/168* (2013.01);
(Continued)

(58) Field of Classification Search
CPC ............ A61M 1/1656; A61M 1/1613; A61M 1/1609; A61M 1/1607; A61M 1/1617; A61M 1/16; A61M 1/1647; A61M 1/3403; A61M 5/168; A61M 5/16831; A61M 5/172; A61M 5/1723; A61M 2005/1726; A61M 2205/33; A61M 2205/3327; A61M 2210/12; A61M 2230/20; A61M 2230/65; A61B 5/145; A61B 5/14546; A61B 5/1468; A61B 5/1473
See application file for complete search history.

(56) References Cited

U.S. PATENT DOCUMENTS

| 4,508,622 | A | | 4/1985 | Polaschegg et al. |
| 5,024,756 | A | * | 6/1991 | Sternby ......................... 210/93 |

(Continued)

FOREIGN PATENT DOCUMENTS

| EP | 0 097 366 | 1/1984 |
| EP | 0 330 892 | 9/1989 |

(Continued)

*Primary Examiner* — Adam Marcetich
(74) *Attorney, Agent, or Firm* — K&L Gates LLP

(57) ABSTRACT

Dialysis apparatus including a blood treatment unit having a dialysate chamber and a blood chamber separated by a semipermeable membrane, a dialysate circuit presenting a supply line and a discharge line connected to the blood treatment unit, a preparation device for preparing a dialysate containing a substance present in the blood too and a regulator regulating the concentration of the substance in the dialysate. A blood circuit to circulate extracorporeal blood through the blood chamber; a controller that determines a value representative of the concentration of the substance in the blood and are programmed for driving the regulator as a function of the determined value representative of the substance concentration in the blood such that the substance concentration in the dialysate tends towards the substance concentration in the blood.

23 Claims, 1 Drawing Sheet

(51) Int. Cl.
*A61M 5/168* (2006.01)
*A61M 5/172* (2006.01)

(52) U.S. Cl.
CPC ........... *A61M 5/16831* (2013.01); *A61M 5/172* (2013.01); *A61M 5/1723* (2013.01); *A61M 2005/1726* (2013.01); *A61M 2205/33* (2013.01); *A61M 2205/3327* (2013.01); *A61M 2210/12* (2013.01); *A61M 2230/20* (2013.01); *A61M 2230/65* (2013.01)

(56) References Cited

U.S. PATENT DOCUMENTS

| | | | |
|---|---|---|---|
| 5,100,554 A | | 3/1992 | Polaschegg |
| 5,567,320 A | | 10/1996 | Goux et al. |
| 6,123,847 A | | 9/2000 | Bene |
| 6,156,002 A | * | 12/2000 | Polaschegg et al. ......... 604/4.01 |
| 6,284,141 B1 | * | 9/2001 | Shaldon et al. ............... 210/739 |
| 6,325,774 B1 | * | 12/2001 | Bene et al. .................... 604/4.01 |
| 6,623,442 B2 | * | 9/2003 | Bene et al. .................... 604/4.01 |
| 6,648,845 B1 | * | 11/2003 | Gotch et al. .................. 604/5.01 |
| 6,860,866 B1 | * | 3/2005 | Graf et al. ..................... 604/5.01 |
| 2001/0004523 A1 | * | 6/2001 | Bosetto et al. ..................... 435/4 |
| 2001/0037968 A1 | | 11/2001 | Bene et al. |
| 2003/0029797 A1 | * | 2/2003 | Govoni et al. ................. 210/646 |
| 2005/0133449 A1 | * | 6/2005 | Sternby ......................... 210/645 |
| 2005/0242034 A1 | | 11/2005 | Connell et al. |
| 2005/0284815 A1 | * | 12/2005 | Sparks et al. .................. 210/645 |
| 2007/0135750 A1 | * | 6/2007 | Kraemer ...................... 604/6.09 |
| 2008/0296226 A1 | | 12/2008 | Gotch |
| 2012/0018379 A1 | * | 1/2012 | Gross et al. ................... 210/647 |

FOREIGN PATENT DOCUMENTS

| | | |
|---|---|---|
| EP | 0 428 927 | 5/1991 |
| EP | 0 547 025 A1 | 6/1993 |
| EP | 1 389 475 A2 | 2/2004 |
| EP | 1 776 972 A1 | 4/2007 |
| EP | 1 810 703 A1 | 7/2007 |

\* cited by examiner

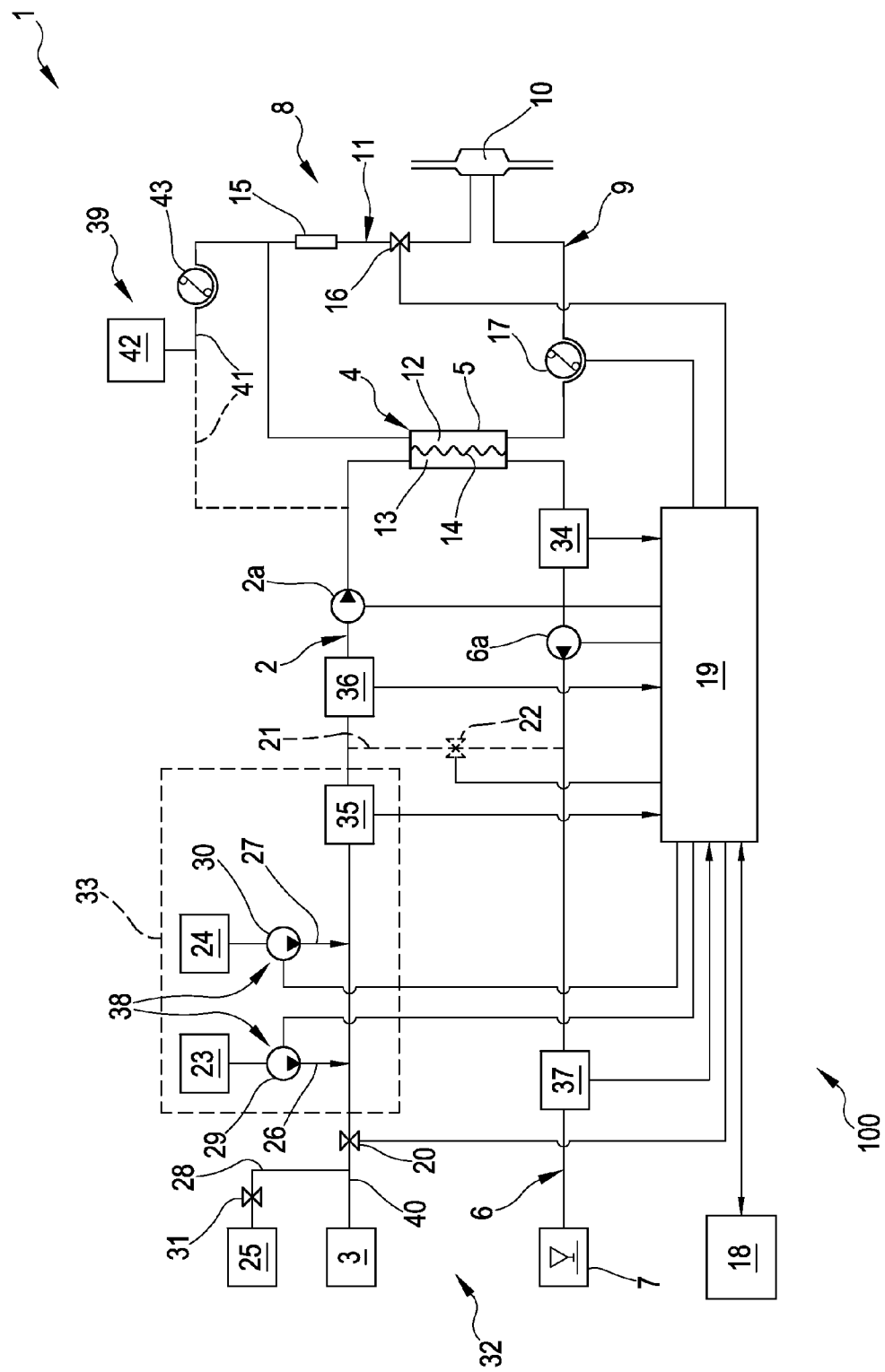

DIALYSIS APPARATUS AND METHOD FOR CONTROLLING A DIALYSIS APPARATUS

TECHNICAL FIELD

The invention relates to a dialysis apparatus and a method for controlling the dialysis apparatus. In particular the invention may be used for regulating the conductivity of a dialysis liquid (or dialysate) during a dialysis or hemodiafiltration treatment.

In more detail the dialysis apparatus and the process are particularly adapted for properly regulating the concentration of sodium in the fresh dialysis liquid.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (sodium, potassium, magnesium, calcium, bicarbonates, phosphates, chlorides) and the regulation of the acid/base equilibrium within the body, which is obtained in particular by the removal of weak acids (phosphates, monosodium acids) and by the production of ammonium salts.

In individuals who have lost the use of their kidneys, since these excretion and regulation mechanisms no longer work, the body accumulates water and waste from the metabolism and exhibits an excess of electrolytes (in particular sodium), as well as, in general, acidosis, the pH of the blood plasma shifting towards 7 (the blood pH normally varies within narrow limits of between 7.35 and 7.45).

In order to overcome renal dysfunction, resort is conventionally made to a blood treatment involving extracorporeal circulation through an exchanger having a semipermeable membrane (haemodialyser) in which the patient's blood is circulated on one side of the membrane and a dialysis liquid, comprising the main electrolytes of the blood in concentrations close to those in the blood of a healthy subject, is circulated on the other side.

Furthermore, a pressure difference is created between the two compartments of the haemodialyser which are delimited by the semipermeable membrane, so that a fraction of the plasma fluid passes by ultrafiltration through the membrane into the compartment for the dialysis liquid.

The blood treatment which takes place in a haemodialyser as regards waste from the metabolism and electrolytes results from two mechanisms of molecular transport through the membrane.

On the one hand, the molecules migrate from the liquid where their concentration is higher to the liquid where their concentration is lower. This is diffusive transport or dialysis.

On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as haemodialysis).

As regards the regulation of the acid/base equilibrium inside the body, the approach adopted to overcome renal deficiency is to act on a mechanism by which the acid/base equilibrium inside the body is regulated, this mechanism consisting of the buffer systems of the blood, the main one of which comprises carbonic acid, as a weak acid, associated with its alkali salt, bicarbonate. This is why, in order to correct acidosis in a patient suffering from renal insufficiency, he is administered with bicarbonate via the vascular route, directly or indirectly, during a haemodialysis session.

The administration is indirect when the bicarbonate is involved in the composition of the dialysis liquid and passes into the blood by diffusion.

One drawback of this method is connected with the fact that bicarbonate precipitates with calcium and magnesium, which belong to the conventional components of a dialysis liquid.

In order to limit this reaction, an acid (acetic acid) is added to the dialysis liquid in order to lower its pH, which has the side effect of increasing the partial pressure of carbon dioxide in it, and has the undesirable consequence of inducing in the patient the discomfort resulting from the excess of this gas in his blood. Furthermore, in view of the maximum acceptable concentration of acid in the dialysis liquid, calcium deposits are produced in the circuits of the dialysis machine, and these need to be removed.

The administration of the bicarbonate is direct when the dialysis liquid is free of bicarbonate and the patient is infused with a sodium bicarbonate solution. This method has the benefit that it avoids having to combine, in the same treatment liquid, the substances which precipitate in the absence of acid.

However, it poses the problem of regulating the sodium concentration in the dialysis liquid so that the patient's body tends towards a determined sodium concentration. This is because, when the patient is infused with sodium bicarbonate with a view to reaching a determined bicarbonate concentration inside the patient's body, an amount of sodium is introduced therein which has not to date been taken into consideration, or has been taken into consideration only empirically, when the sodium concentration of the dialysis liquid is fixed.

In other words, with the above cited existing systems used for implementing the method which has just been described, no provision is made for regulating both the infusion flow rate of the sodium bicarbonate solution and the sodium concentration of the dialysis liquid such that the patient's body tends towards a precise predetermined concentration both of bicarbonate and of sodium.

To solve the above mentioned drawbacks, the prior art comprises dialysis apparatus wherein the dialysate conductivity is controlled in order to reach a desired post-dialysis plasmatic conductivity, i.e. conductivity (or sodium concentration) of the patient's blood at the end of the dialysis treatment.

It is known, for example from EP 1389475, a dialysis apparatus provided with a conductivity system that computes the dialysate conductivity (corresponding to the dialysate sodium concentration) from periodic measurements of the sodium blood concentration allowing the sodium level of the patient to reach a prescribed end-of-session value.

This dialysis apparatus includes a device for preparing a dialysis liquid containing sodium having a pump for regulating the sodium concentration and a dialysis liquid circuit with a feed line and a discharge line; the feed line has one end connected to the device for preparing a dialysis liquid and another end connected to a dialyser.

The discharge line has, as well, an end connected to the dialyser, it is also provided a bag and a pump for infusing a patient with an infusion solution containing sodium at a determined and known concentration.

A structure for determining the sodium concentration [Na+]$_{dial}$ of the dialysis liquid is also provided so that the patient's body tends towards a desired sodium concentration [Na+]$_{des}$, as a function of the dialysance D for sodium of the dialyser, of the desired sodium concentration [Na+]$_{des}$ inside the patient's body, of the infusion flow rate and of the sodium concentration [Na+]$_{sol}$ of the infusion solution.

A control unit drives the pump for regulating the sodium concentration of the dialysis liquid such that this concentration is equal (tends towards) to the determined concentration [Na+]$_{dial}$.

One of the problems of the dialysis apparatus of the prior art is presently the choice of the appropriate post-dialysis plasmatic conductivity target.

SUMMARY

An aim of the present invention is providing a dialysis apparatus able to automatically perform a proper setting of the dialysate content of a substance, particularly an ionic substance, present in the blood as well.

In detail it is an aim of the present invention to provide a dialysis apparatus able to automatically perform a proper setting of the dialysate conductivity.

A further aim of the invention is to make available a dialysis apparatus able to provide an automated delivery and control of the dialysis prescription, particularly in order to restore at each dialysis session the proper sodium-water equilibrium to the patient.

At least one of the above-indicated aims is attained by an apparatus and a corresponding method as in one or more of the appended claims, taken singly or in any combination.

The invention relates to a dialysis apparatus having a blood treatment unit comprising a dialysate chamber and a blood chamber separated by a semipermeable membrane; a dialysate circuit comprising a supply line and a discharge line connected to said blood treatment unit, respectively, upstream and downstream of said dialysate chamber; a preparation device for preparing a dialysate containing a substance, said substance being present in the blood too, said preparation device being connected to said supply line; a blood circuit configured to circulate extracorporeal blood through said blood chamber; control means for determining a value representative of the concentration of said substance in the blood in said blood circuit, the control means being programmed for performing the step of driving said regulating means as a function of the determined value representative of the substance concentration in the blood such that the substance concentration in the dialysate tends towards the determined substance concentration in the blood, particularly in case the determined sodium concentration or determined conductivity is within a predefined range of sodium concentration values or conductivity values.

In a further aspect of the invention said substance is a ionic substance, e.g. sodium, and the control means are programmed for determining a value representative of the concentration of said ionic substance in the blood in said blood circuit, the preparation device preparing a dialysate containing the ionic substance, e.g. sodium, said preparation device comprising regulating means for regulating the ionic substance concentration, e.g. the sodium concentration, in the dialysate, said control means being programmed for determining a value representative of the concentration of the ionic substance, e.g. sodium, in the blood in said blood circuit and being programmed for driving said regulating means as a function of the determined value representative of the ionic substance concentration, e.g. sodium concentration, in the blood such that the ionic substance concentration, e.g. sodium concentration, in the dialysate tends towards the ionic substance concentration, e.g. sodium concentration, in the blood.

According to another feature of the invention, the apparatus further comprises a conductivity sensor arranged in said discharge line, the control means is programmed for determining a value representative of the concentration of said ionic substance in the blood in said blood circuit at least from conductivity values measured by said conductivity sensor.

A further solution proposed by the invention is using the actual value of the plasmatic conductivity as the target value for controlling the dialysate conductivity. The actual plasmatic conductivity value may be the pre-dialysis plasmatic conductivity measured at the start of the dialysis session, or the plasmatic conductivity measured in the course of the dialysis session.

In an embodiment, the plasmatic conductivity may be determined, in a known manner, from the conductivity values measured or determined in the dialysate circuit upstream and downstream the dialyzer, after and before a change of the dialysate conductivity.

The target value of the dialysate conductivity DC may be set at the actual value of the plasmatic conductivity PC if $DC_{min} < PC < DC_{max}$, where $DC_{min}$ and $DC_{max}$ are two threshold values which are pre-defined and memorized and which may be equal to, for example, respectively, 13.5 mS/cm and 14.5 mS/cm. The dialysate conductivity DC may be set at the minimum threshold value $DC_{min}$ if $PC < DC_{min}$. The dialysate conductivity may be set at the maximum threshold value $DC_{max}$ if $PC > DC_{max}$.

The plasmatic ionic conductivity of the patient may be periodically calculated during the dialysis treatment, for example at every 15 minutes, and the setting of the dialysate conductivity may be updated accordingly.

Thanks to the invention a dialysis monitor modality with a proper setting of the dialysate conductivity in order to achieve an individualized control of the patient sodium level may be provided. Moreover an automated, safe and simple control mode for controlling a dialysis apparatus is also made available.

An advantage of the invention is a better patient care by providing clinical benefits in fragile patients, such as, for example, a good tolerance of weight loss in patients with high plasma conductivity at the start of the dialysis session with possibility of a further reduction of the dry weight. Another benefit to the patient may be a reduction of hypertensive episodes in patients with low plasma conductivity at the start of the session.

A further advantage is economics for the hospitals/clinics by avoiding clinical complications. Moreover the dialysis apparatus may be totally managed by the nurses after a relatively short education.

One or more of these aims and advantages and more besides are attained by the object of the invention, according to one or more of the appended claims.

Further characteristics and advantages of the present invention will better emerge from the detailed description that follows of at least an embodiment of the invention, illustrated by way of non-limiting example in the accompanying FIGURES of the drawings.

BRIEF DESCRIPTION OF THE DRAWINGS

The description will now follow, with reference to the only appended FIGURE, provided by way of non-limiting example, in which:

FIG. 1 schematically represents a dialysis apparatus made according to an illustrating embodiment.

DETAILED DESCRIPTION

FIG. 1 illustrates a dialysis apparatus 100 in an embodiment of the invention comprising a hydraulic circuit 1.

An example of the hydraulic circuit 1 is schematically illustrated, but it is to be noted that the specific structure of the hydraulic circuit 1 is not relevant for the purposes of the present invention and therefore other and different circuits to those specifically shown in FIG. 1 might be used in consequence of the functional and design needs of each single medical apparatus.

The hydraulic circuit 1 exhibits a dialysate circuit 32 presenting at least one supply line 2, destined to transport a treatment liquid from at least one source 3 towards a treatment station 4 where one or more blood treatment units 5 operate.

The dialysate circuit 32 further comprises at least one discharge line 6, destined for the transport of a used liquid (spent dialysate and liquid ultrafiltered from the blood through the membrane 14) from the treatment station 4 towards an evacuation zone, schematically denoted by 7 in FIG. 1.

The hydraulic circuit cooperates with a blood circuit 8, also schematically represented in FIG. 1 in its basis component parts. The specific structure of the blood circuit is also not fundamental, with reference to the present invention. Thus, with reference to FIG. 1, a brief description of a possible embodiment of a blood circuit is made, which is however provided purely by way of non-limiting example.

The blood circuit 8 of FIG. 1 comprises a withdrawal line 9 designed to remove blood from a vascular access 10 and a return line 11 designed to return the treated blood to the vascular access.

The blood circuit of FIG. 1 further comprises a first chamber, or blood chamber, 12 of the blood treatment unit 5, the second chamber 13 of which is connected to the hydraulic circuit 1.

In greater detail the withdrawal line is connected at the inlet to the blood chamber 12, while the return line is connected at the output to the blood chamber 12.

In turn, the supply line 2 is connected at the inlet to the second chamber 13, while the discharge line 6 is connected at the outlet to the second chamber.

The blood treatment unit 5, for example a dialyzer or a plasma filter or a hemofilter or a hemodiafilter, comprises, as mentioned, the two chambers 12 and 13 which are separated by a semipermeable membrane 14, for example of the hollow-fibre type or plate type.

The blood circuit can also comprise one or more separators 15: in the example of FIG. 1 a separator 15 is included at the return line 11, upstream of a safety valve 16. The valve 16 can be activated to close the return line when, for example, for security reasons the blood return to the vascular access 10 has to be halted.

The dialysis apparatus 1 can also comprise one or more blood pumps 17, for example positive displacement pumps such as peristaltic pumps; in the example of FIG. 1, a pump 17 is included on the withdrawal line 9.

The apparatus of above-described embodiment can also comprise a user interface 18 and control means 19, i. e. a programmed/programmable control unit, connected to the user interface.

The control means 19 can for example comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the medical apparatus may also comprise a closing device operating for example in the supply line and commandable between one first operating condition, in which the closing device allows a liquid flow along the supply channel towards the treatment zone, and a second operative position, in which the closing device blocks passage of liquid towards the treatment zone.

In this case, the control unit 19 can be connected to the closing device and programmed to drive the closing device to pass from the first to the second operative condition, should an alarm condition have been detected.

In FIG. 1 the closing device is a solenoid valve 20 controlled by the unit 19 as described above. Obviously a valve of another nature, either an occlusive pump or a further member able to selectively prevent and enable fluid passage can be used.

Alternatively or additionally to the valve 20, the closing device can also comprise a bypass line 21 which connects the supply line and the discharge line, and one or more fluid check members 22 connected to the control unit for selectively opening and closing the bypass channel and the supply channel downstream of the bypass channel. The components 21 and 22, which can be alternative or additional to the presence of the member 20 are represented by a broken line in FIG. 1.

The check members 22 on command of the control unit close the fluid passage towards the treatment zone and connect the source with the discharge channel through the bypass line.

Again with the aim of controlling the fluid passage towards the unit 4, pumps 2a and 6a can be included, located respectively on the lines 2 and 6 and also operatively connected to the control unit 19.

The apparatus also comprises a dialysate preparation device 33 which may be of any known type, for example including one or more concentrate sources 23, 24 and respective pumps 29, 30 for the delivery, as well as a conductivity sensor 35.

Of course other kinds of dialysate preparation devices 33 might be equivalently used, having a single or further concentrate sources and/or a single or more pumps.

Since the dialysis apparatus may comprise various liquid sources (for example one or more water sources 3, one or more concentrate sources 23, 24, one or more sources of disinfectant liquids 25) connected to the supply channel 2 with respective delivery lines 26, 27 and 28, the apparatus may exhibit, at each delivery line, a respective check member, not shown and, for example, comprising a valve member and/or an occlusive pump.

The preparation device 33 may be any known system configured for on-line preparing dialysate from water and concentrates.

The supply line 2 connects the blood treatment unit 5 to the preparation device 33 for preparing dialysate. The preparation device 33 may be, for example, the one described in the U.S. Pat. No. 6,123,847 the content of which is herein incorporated by reference.

As shown, the supply line 2 connects the device 33 for preparing dialysis liquid to the blood treatment unit 5 and comprises a main line 40 whose upstream end is intended to be connected to a source 3 of running water.

Delivery line/s 26/27 is/are connected to this main line 40, the free end of which delivery line/s is/are intended to be in fluid communication (for example immersed) in a container/s 23, 24 for a concentrated saline solution each containing sodium chloride and/or calcium chloride and/or magnesium chloride and/or potassium chloride.

Pump/s 29, 30 is/are arranged in the delivery line/s 26/27 in order to allow the metered mixing of water and concentrated solution in the main line 40. The pump/s 29, 30 is/are driven on the basis of the comparison between 1) a target conductivity value for the mixture of liquids formed where the main line 40 joins the delivery line/s 26/27, and 2) the value of the conductivity of this mixture measured by means of a conductivity sensor 35 arranged in the main line 40 immediately downstream of the junction between the main line 40 and the delivery line/s 26/27.

Therefore, as mentioned, the dialysate may contain, for example, ions of sodium, calcium, magnesium and potassium and the preparation device 33 may be configured to prepare the dialysate on the basis of a comparison between a target conductivity value and an actual conductivity value of the dialysate measured by a conductivity sensor 35 of the device 33.

The preparation device 33 comprises regulating means 38, of a known type (i.e. pump/s), which is configured to regulate the concentration of a specific substance, in particular an ionic substance, in the dialysis liquid. Generally it is advantageous to control the sodium concentration of the dialysate.

The supply line 2 forms an extension of the main line 40 of the device 33 for preparing dialysis liquid. Arranged in this supply line, in the direction in which the liquid circulates, there are the first flow meter 36 and the circulation pump 2a.

The discharge line 6 may be provided with a further circulation pump 6a and a further flow meter 37. The flow meters 36, 37 may be used to control (in a known manner) the fluid balance of a patient connected to the blood circuit 8 for a dialysis session.

The conductivity sensor 34, which is connected to the discharge line 6, is configured to detect conductivity values of the discharge liquid downstream of the blood treatment unit 5.

The dialysis apparatus represented in FIG. 1 also comprises the calculation and control unit 19. This unit 19 may be connected to a (graphic) user interface 18 through which it may receive instructions, for example target values, such as blood flow rate $Q_b$, dialysate flow rate $Q_d$, infusion liquid flow rate $Q_{inf}$ (where appropriate), patient weight loss WL. The calculation and control unit 19 furthermore may receive detected values by the sensors of the apparatus, such as the aforementioned flow meters 36, 37, the conductivity sensor 35 of the device 33 and the conductivity sensor 34 in the discharge line 6. On the basis of the instructions received and the operating modes and algorithms which have been programmed, the unit 19 drives the actuators of the apparatus, such as the blood pump 17, the aforementioned circulation pumps 2a, 6a, and the preparation device 33.

As already mentioned, the described embodiments are intended to be non-limiting examples. In particular the circuits of FIG. 1 should not be interpreted as defining or limiting, as an apparatus such as in the invention can comprise other additional or alternative components to those described.

For example an ultrafiltration line can be included, with at least one respective pump connected to the discharge line 6.

One or more infusion lines can also be included, with respective pumps or flow regulation valves, the infusion lines being connected up to the return line 11 and/or the withdrawal line 9 and/or directly to the patient. The liquid sources can be pre-packaged bags and/or liquids prepared by the apparatus itself.

Furthermore one or more devices for measuring specific substance concentrations might be implemented either (or both) in the dialysate side or (and) in the blood side of the hydraulic circuit. Concentration of calcium, potassium, magnesium and/or sodium might be desired to be known.

Finally, the above-cited one or more pumps 2a, 6a and all the necessary temperature, pressure and concentration sensors can operate either on the supply line 2 or on the discharge line 6, in order to adequately monitor the preparation and movement of the liquid in the hydraulic circuit.

The dialysis apparatus above described operates as follows.

The extracorporeal blood circuit 8 is connected to the patient, the blood pump 17 is turned on at a predetermined delivery rate $Q_b$, and the extracorporeal blood flows through the blood chamber 12.

At the same time, the preparation device 33 delivers the dialysate at a predetermined delivery rate $Q_d$ and at a predetermined sodium concentration (that is to say also a conductivity) to the dialysate chamber 13.

Notice in this respect that if a substance is an ionic substance, then the concentration of the substance influences the conductivity of the dialysis liquid; in particular considering that conductivity is largely influenced by the concentration of sodium ions, than measure/calculation of conductivity values gives an indication of sodium concentration in blood and in the dialysis liquid. As conductivity sensors are much more convenient and easy to use than ion selective sensors for directly detecting the concentration of an electrolyte in a liquid flow, conductivity measurements are in particular used. Therefore in the present description each time the sodium concentration in a fluid (in the blood, in the fresh dialysis fluid, in the substitution fluid . . . ) is mentioned it is equivalently intended the conductivity of said fluid and vice versa.

In its general aspect the control means 19 are configured and programmed to determine a concentration of a substance in the blood, particularly at least during the first phases of the dialisys treatment (as soon as the flow rates and the other operative conditions are stable allowing the correct substance concentration measurement). The mentioned substance is a substance which is also included in the fresh dialysis liquid.

In other terms the control means 19 may determine a value representative of the concentration of said substance. This representative value could be, for example, the conductivity value of the blood which represents the sodium concentration in the blood, or could also be directly the sodium concentration in the blood.

The actuators of the dialysis apparatus are controlled, in a known manner, so that the ultrafiltration rate of the plasma fluid across the semipermeable membrane 14 is equal to the desired weight loss rate plus, eventually, the rate of the infusate injected into the extracorporeal blood.

The regulating means 38 is driven, as a function of the measured value representative of the substance concentration in the blood, in order to achieve a similar (tending to be equal) concentration of the same substance in the dialysate.

Indeed if the value is the conductivity of the blood, the regulating means operates so that the conductivity in the fresh dialysis liquid tends towards the same value as the one measured in the blood and consequently the sodium concentration tends to be equal to the sodium concentration in the blood.

It is clear that the substance whose concentration is to be measured in the blood and regulated in the dialysate is optionally an ionic substance (Calcium, Magnesium, Potassium, Sodium) whose concentration might be estimated through conductivity measurements or directly through specific concentration measurements; of course the sodium concentration is generally, but not exclusively, the substance intended to be measured and regulated.

In the description reference will be made in non-limiting examples to sodium.

The concentration of sodium in the blood is determined in a known manner, for example by using the method described in the U.S. Pat. No. 5,567,320 which is herein incorporated by reference, or the method described in the European Patent No. EP 547025 which is herein incorporated by reference. Any other method or device for determining the concentration of sodium in the blood from measurements of the dialysate conductivity may be used. In brief, the calculation and control unit 19 is programmed to calculate the sodium concentration of the blood on the basis of at least two conductivity values determined respectively upstream and downstream of the dialysate chamber in at least two successively dialysates prepared, by the device 33, with different concentrations of sodium. A formula, which can be used for this calculation, is known, for example, by the aforementioned U.S. Pat. No. 5,567,320 or by EP 547025.

Then the regulating means 38 of the preparation device 33 is driven by the calculation and control unit 19 such that the sodium concentration of the dialysate is equal (or substantially equal) to the sodium concentration of the blood which has been determined.

It is clear that regulating the preparation device for obtaining a sodium concentration means that the sodium concentration of the dialysate tends towards the expected value, being of course possible small variation or differences with respect to the exact expected concentration value. In other terms by the wording equal (or substantially equal) it is intended that the set value will be the one desired and that the regulating means will adjust the dialysate concentration value (measured through the mentioned conductivity sensor) so as to be as close as possible to the set value (ideally being equal to such set value).

In the specific and advantageous embodiment, the described regulating means 38 is driven by the calculation and control unit 19 such that the sodium concentration of the dialysate is equal (or substantially equal) to the sodium concentration of the blood which has been determined at the start of the dialysis session.

In other terms a conductivity measure of the blood is performed at the beginning of the treatment session and the first (or second) reliable measure of the blood conductivity is set as the target value for the dialysate conductivity. Generally the first (or second) reliable measure of the blood conductivity is obtained within about 30 min from the dialysis session beginning.

Therefore the plasmatic conductivity measured at the session start (also called pre-dialysis plasmatic conductivity) is automatically set by the control unit 19 and used as the target (actual) conductivity value for the fresh dialysis liquid.

More particularly, the unit 19 may be programmed for driving the regulating means 38 such that the sodium concentration of the dialysate is equal to the determined sodium concentration of the blood if the determined sodium concentration of the blood is comprised within a predetermined range between a minimum and maximum prefixed thresholds, corresponding to a certain range of conductivities, for example between 13.5 mS/cm and 14.5 mS/cm, or is equal to the minimum threshold if the determined sodium concentration of the blood is less or equal to the minimum threshold (corresponding to a conductivity value of 13.5 mS/cm), or is equal to the maximum threshold if the determined sodium concentration of the blood is greater or equal to the maximum threshold (corresponding to a conductivity value of 14.5 mS/cm).

The automated setting of the concentration of sodium in the dialysate (corresponding to the dialysate conductivity) as above described may be repeated periodically during the treatment, for example at every 15 minutes, or upon a request of the user.

If an infusate is injected into the extracorporeal blood, the infusion device 39 will comprise an infusate circuit that may be connected to the dialysate circuit 41 such that a fraction of the dialysate flow, which is diverted from the supply line 2, is treated in a known manner and then injected into the blood (in on-line hemodiafiltration mode). In this manner the infusate will have the same chemical composition of the dialysate.

The infusate may be supplied, for example in off-line hemodiafiltration mode, from a source of infusate 42 not connected to the source of dialysate (e.g. a source of batch type). The infusate may have a different composition than the dialysate.

The infusate may contain sodium (at a different concentration than the dialysate) and may contain a further substance A (for example bicarbonate) which may be absent in the dialysate.

The infusion device 39 may be driven by the unit 19 so that the concentration of the further substance A (e.g. bicarbonate) inside the patient's body evolves approximately towards a desired concentration $A_{des}$. In particular, the flow rate $Q_{inf}$ of the infusate into the blood may be calculated and adjusted regularly, by adjusting speed of infusate pump 43, for example, so that the concentration of the further substance A in the blood tends precisely towards a desired value $A_{des}$.

When an infusate is injected (e.g. downstream the dialyzer), the preparation device 33 may be adjusted so that the sodium concentration $Na_{dial}$ of the dialysate is equal to the sodium concentration $Na_b$ of the extracorporeal blood. As an alternative, if the infusate has a concentration of sodium equal to $Na_{sol}$ (wherein $Na_{sol}$ is predefined and known) and is injected at a flow rate equal to $Q_{inf}$, then the dialysate preparation device 33 may be driven such that the sodium concentration $Na_{dial}$ of the dialysate is equal to $$Na_{dial}=Na_b+Q_{inf}*(Na_b-Na_{sol})/D$$

where $Na_b$ is the actual sodium concentration of blood and D is the dialysance of the blood treatment unit 5 for sodium ($Na_b$ and D may be calculated as taught, for example, by U.S. Pat. No. 5,567,320 or EP 547025). The quantity $Q_{inf}*(Na_b-Na_{sol})/D$ may be considered a correction factor which can be added to $Na_b$ when an infusate with a sodium concentration different than the sodium concentration of the dialysate is injected into the blood.

The flow rate $Q_{ref}$ of the infusate may be calculated (at any instant) by applying the formula:

$$Q_{inf}=Cl*A_{des}/(A_{sol}-A_{des})$$

where $Q_{inf}$ is the infusion flow rate, Cl is the clearance of the dialyzer for the substance A (e.g. bicarbonate), $A_{sol}$ is the concentration of the substance A (e.g. bicarbonate) in the dialysate, $A_{des}$ is the desired concentration of the substance A (e.g. bicarbonate) inside the patient's body at the end of the treatment session. As known, the clearance Cl of the blood treatment unit 5 for a substance (e.g. bicarbonate) can be readily extrapolated from the dialysance D for sodium, which can be calculated in a known manner (see for example U.S. Pat. No. 6,123,847, U.S. Pat. No. 5,567,320, EP 547025).

The above formulas of $Na_{dial}$ and $Q_{inf}$ do not apply only to a dialysis or hemodiafiltration method in which the infusate comprises sodium bicarbonate and the dialysate is free thereof. It may be applied, for example, to any dialysis or hemodiafiltration method in which the dialysate contains sodium and the infusate contains a sodium salt (sodium and a substance A as bicarbonate or possibly other than bicarbonate). By way of example, the dialysate prepared by the device 33 may contain sodium and bicarbonate, and optionally potassium, and the infusate may contain sodium and magnesium and/or calcium, and optionally potassium (these compositions of dialysate and infusate is particularly suited for hemodiafiltration).

The unit 19 may be programmed such that the user may select, by means of the user interface 18, to drive the preparation device 33 in at least two modes: a first mode (Conductivity control isonatric mode) as above described in which the dialysate conductivity (or dialysate sodium concentration) is automatically set to be equal to the actual blood conductivity (or actual blood sodium concentration) with the optional addition of the above correction factor, a second mode (Conductivity control mode) in which the dialysate conductivity (or dialysate sodium concentration) is automatically set to allow the blood conductivity (or blood sodium concentration) of the patient to reach a predefined value (at the end of the dialysis session). It may be possible a third mode (preset mode) in which the dialysate conductivity (or dialysate sodium concentration) is equal to a predefined (constant) value or a profile of (time variable) values. The unit 19 may be programmed to allow the user, by means of the user interface 18, to switch from a mode to another one.

The invention claimed is:

1. A dialysis apparatus comprising:
   a blood treatment unit comprising a dialysate chamber and a blood chamber separated by a semipermeable membrane;
   a dialysate circuit comprising a supply line and a discharge line connected to said blood treatment unit, respectively, upstream and downstream of said dialysate chamber;
   a preparation device configured to prepare a dialysate containing a substance which is also present in blood, the preparation device includes a regulator configured to regulate a concentration of the substance in dialysate, said preparation device being connected to said supply line;
   a blood circuit configured to circulate extracorporeal blood through said blood chamber;
   a controller configured to determine a value representative of the concentration of said substance in the blood and configured to drive the regulator as a function of the determined value representative of the substance concentration in the blood,
   wherein the controller causes the preparation device to regulate the concentration of the substance in the dialysate to tend towards at least one of:
   (i) the determined concentration of the substance in the blood if the determined concentration of the substance in the blood is greater than a minimum threshold, and
   (ii) the minimum threshold if the determined concentration of the substance in the blood is less than the minimum threshold, and
   wherein the controller causes the preparation device to regulate the concentration of the substance in the dialysate to tend towards at least one of:
   (iii) the determined concentration of the substance in the blood if the determined concentration of the substance in the blood is less than a maximum threshold, and
   (iv) the maximum threshold if the determined concentration of the substance in the blood is greater than the maximum threshold.

2. The apparatus according to claim 1, wherein said substance is an ionic substance, the preparation device prepares dialysate containing the ionic substance, said regulator regulates the ionic substance concentration in the dialysate, and said controller causes the regulator to regulate the concentration as a function of the determined value such that the ionic substance concentration in the dialysate tends towards the ionic substance concentration in the blood.

3. The apparatus according to claim 2, wherein said ionic substance is sodium.

4. The apparatus according to claim 2, further comprising a conductivity sensor arranged in said discharge line, wherein the controller determines a value representative of the concentration of said ionic substance in the blood in said blood circuit at least from conductivity values measured by said conductivity sensor.

5. The apparatus according to claim 1, comprising an infusion device connected to said blood circuit for injecting an infusate into said blood circuit, and wherein, if the ionic substance concentration in the infusate is different than the ionic substance concentration in the dialysate, said regulator regulates the ionic substance concentration in the dialysate to be equal to the determined ionic substance concentration in the blood plus a correction factor that depends on the ionic substance concentration in the blood and the ionic substance concentration in the infusate.

6. The apparatus according to claim 5, wherein said correction factor depends on: (i) the sodium concentration or conductivity of the blood minus the sodium concentration or conductivity of the infusate, (ii) a flow rate Qinf of the infusate into said blood circuit, and (iii) a dialysance D for sodium of said blood treatment unit.

7. The apparatus according to claim 1, wherein said controller executes instructions to:
   determine the conductivity of the dialysate upstream and downstream of said dialysate chamber; and
   calculate the sodium concentration of the blood from at least two conductivity values determined respectively upstream and downstream of said blood treatment unit in at least two successively prepared dialysates with different concentrations of sodium.

8. The apparatus according to claim 7, wherein said controller executes instructions to cause the regulator to regulate the concentration at least twice and at predetermined times during a dialysis treatment.

9. The apparatus according to claim 1, wherein the controller executes instructions to cause the regulator to regulate the sodium concentration or the conductivity of the dialysate to tend at least towards a pre-dialysis sodium concentration or towards a pre-dialysis conductivity of the blood.

10. The apparatus according to claim 1, wherein control means are programmed for performing the step of driving said regulating means such that the sodium concentration or the conductivity of the dialysate tends at least towards a pre-dialysis sodium concentration or towards a pre-dialysis conductivity of the blood in case the determined pre-dialysis sodium concentration or determined pre-dialysis conductivity is within a predefined range of sodium concentration values or conductivity values.

11. The apparatus according to claim 1, wherein control means are programmed for performing the step of driving said regulating means such that the sodium concentration or the conductivity of the dialysate tends at least towards a pre-dialysis sodium concentration or towards a pre-dialysis conductivity of the blood measured at the start of the dialysis session.

12. The apparatus according to claim 1, wherein control means are programmed for performing the step of driving said regulating means such that the sodium concentration or the conductivity of the dialysate tends at least towards a pre-dialysis sodium concentration or towards a pre-dialysis conductivity of the blood measured in the course of the dialysis session.

13. The apparatus according to claim 1, wherein control means are programmed for performing the step of driving said regulating means such that the sodium concentration or the conductivity of the dialysate tends at least towards a pre-dialysis sodium concentration or towards a pre-dialysis conductivity of the blood, and wherein the pre-dialysis sodium concentration or the pre-dialysis conductivity of the blood is measured within 30 min from a dialysis session beginning.

14. A method of controlling a dialysis apparatus, the dialysis apparatus including:
   a blood treatment unit comprising a dialysate chamber and a blood chamber separated by a semipermeable membrane;
   a dialysate circuit comprising a supply line and a discharge line connected to said blood treatment unit, respectively, upstream and downstream of said dialysate chamber;
   a preparation device for preparing a dialysate containing an ionic substance, said ionic substance being present in the blood too, said preparation device comprising a regulator to regulate the concentration of said ionic substance in the dialysate, said preparation device being connected to said supply line;
   a blood circuit configured to circulate extracorporeal blood through said blood chamber;
   a controller configured to determine a value representative of the concentration of said ionic substance in the blood in said blood circuit and configured to drive said regulator as a function of the determined value representative of the ionic substance concentration in the blood such that the ionic substance concentration in the dialysate tends towards the ionic substance concentration in the blood;
   the method comprising:
   circulating dialysate and blood, respectively, in said dialysate chamber and blood chamber, determining said ionic substance concentration in the blood, and
   wherein the regulator is driven such that the ionic substance concentration of the dialysate tends toward at least one of:
   (i) the ionic substance concentration in the blood if the ionic substance concentration in the blood is greater than a minimum threshold, and
   (ii) the minimum threshold if the ionic substance concentration in the blood is less than the minimum threshold, and
   wherein the regulator regulates the ionic substance concentration of the dialysate to tend toward at least one of:
   (iii) the ionic substance concentration of the blood if the ionic substance concentration of the blood is less than a maximum threshold, and
   (iv) the maximum threshold if the ionic substance concentration of the blood is greater than the maximum threshold.

15. The method according to claim 14, wherein determining the ionic substance concentration in the blood comprises determining a pre-dialysis ionic substance concentration in the blood, and wherein the step of driving comprises regulation the ionic substance concentration in the dialysate to tend toward at least the determined pre-dialysis ionic substance concentration in the blood.

16. The method according to claim 15, wherein the infusate contains sodium and at least one further substance, which is not contained in the dialysate.

17. Method according to claim 16, wherein said infusate is injected at an infusion flow rate determined such that, at an end of a treatment session, the concentration of said at least one further substance inside a patient's body tends towards a desired concentration.

18. The method according to claim 17, wherein said infusion flow rate is determined according to the formula $Qinf=Cl*Ades/(Asol-Ades)$, where Qinf is infusion flow rate, Cl is the clearance of the blood treatment unit for the further substance, Asol is the concentration of the substance in the dialysate, Ades is the desired concentration of the further substance inside the patient's body at the end of the treatment session.

19. The method according to claim 14, comprising the step of injecting an infusate into the extracorporeal blood and wherein, if the ionic substance concentration in the infusate is different than the ionic substance concentration in the dialysate, said regulator regulates the ionic substance concentration in the dialysate to tend toward the determined ionic substance concentration in the blood plus a correction factor that depends on the ionic substance concentration in the blood and the ionic substance concentration in the infusate.

20. The method according to claim 19, wherein said correction factor depends on: (i) the sodium concentration of the blood minus the sodium concentration of the infusate, (ii) a flow rate Qinf of the infusate into said blood circuit, and (iii) a dialysance D for sodium of said blood treatment unit.

21. The method according to claim 14, wherein determining the substance concentration in the blood comprises determining at least one value selected from the group consisting of a pre-dialysis sodium concentration and a pre-dialysis conductivity of the blood, and wherein said driving step regulates the sodium concentration or the conductivity of the dialysate at least towards the determined pre-dialysis sodium concentration or towards the determined pre-dialysis conductivity of the blood measured at the start of the dialysis session.

22. The method according to claim 14, wherein determining the substance concentration in the blood comprises determining at least one value selected from the group consisting of a pre-dialysis sodium concentration and a pre-dialysis conductivity of the blood, and wherein the driving step regulates the sodium concentration or the conductivity of the dialysate to tend at least towards the determined pre-dialysis sodium concentration or towards the determined pre-dialysis conductivity of the blood measured in the course of the dialysis session.

23. The method according to claim 14, wherein determining the substance concentration in the blood comprises determining at least one value selected from the group consisting of a pre-dialysis sodium concentration and a pre-dialysis conductivity of the blood, wherein the driving step regulates the sodium concentration or the conductivity of the dialysate to tend at least towards the determined pre-dialysis sodium concentration or towards the determined pre-dialysis conductivity of the blood, and wherein the determined pre-dialysis sodium concentration or the determined pre-dialysis conductivity of the blood is measured within 30 min from a dialysis session beginning.

* * * * *